US010226544B2

(12) United States Patent
Sasaki et al.

(10) Patent No.: US 10,226,544 B2
(45) Date of Patent: Mar. 12, 2019

(54) MALODOR COUNTERACTING COMPOSITIONS

(71) Applicants: Takashi Sasaki, Matawan, NJ (US); Johan G. L. Pluyter, Middletown, NJ (US); Elizabeth Veliath, Piscataway, NJ (US)

(72) Inventors: Takashi Sasaki, Matawan, NJ (US); Johan G. L. Pluyter, Middletown, NJ (US); Elizabeth Veliath, Piscataway, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 14/731,865

(22) Filed: Jun. 5, 2015

(65) Prior Publication Data
US 2016/0354504 A1 Dec. 8, 2016

(51) Int. Cl.
A23L 5/20 (2016.01)
A61K 8/36 (2006.01)
A61K 8/37 (2006.01)
A61K 8/42 (2006.01)
A61K 8/73 (2006.01)
A61K 8/86 (2006.01)
A61L 9/01 (2006.01)
C11D 3/20 (2006.01)
C11D 3/32 (2006.01)
C11D 3/37 (2006.01)
A61K 8/365 (2006.01)
A61L 9/014 (2006.01)
A61Q 11/00 (2006.01)
A61Q 15/00 (2006.01)
C08K 5/134 (2006.01)
D06M 15/21 (2006.01)
D06M 15/61 (2006.01)
D06M 16/00 (2006.01)
D06M 23/12 (2006.01)
D06M 15/285 (2006.01)

(52) U.S. Cl.
CPC .............. A61L 9/01 (2013.01); A23L 5/27 (2016.08); A61K 8/36 (2013.01); A61K 8/365 (2013.01); A61K 8/37 (2013.01); A61K 8/42 (2013.01); A61K 8/73 (2013.01); A61K 8/86 (2013.01); A61L 9/014 (2013.01); A61Q 11/00 (2013.01); A61Q 15/00 (2013.01); C08K 5/134 (2013.01); C11D 3/2093 (2013.01); C11D 3/32 (2013.01); C11D 3/3707 (2013.01); D06M 15/21 (2013.01); D06M 15/285 (2013.01); D06M 15/61 (2013.01); D06M 16/00 (2013.01); D06M 23/12 (2013.01); A23V 2002/00 (2013.01); A61K 2800/10 (2013.01); A61K 2800/57 (2013.01)

(58) Field of Classification Search
CPC .. A61L 9/01; A61L 9/014; A23L 5/27; D06M 16/00; D06M 15/61; D06M 15/285; D06M 23/12; D06M 15/21; C11D 3/3707; C11D 3/2093; C11D 3/32; A61K 8/36; A61K 8/37; A61K 8/86; A61K 8/73; A61K 8/365; A61K 8/42; A61K 2800/10; A61K 2800/57; A61Q 15/00; A61Q 11/00; C08K 5/134; A23V 2002/00
See application file for complete search history.

(56) References Cited

U.S. PATENT DOCUMENTS

| | | |
|---|---|---|
| 2,475,273 A | 7/1949 | Adelson et al. |
| 2,962,478 A | 11/1960 | Leonard et al. |
| 3,459,852 A | 8/1969 | Roehm |
| 3,580,906 A | 5/1971 | Bernasek et al. |
| 4,579,627 A | 4/1986 | Brailsford |
| 5,037,412 A | 8/1991 | Tanzer et al. |
| 5,288,802 A | 2/1994 | Walters et al. |
| 5,601,809 A | 2/1997 | Davis |
| 5,719,231 A | 2/1998 | Famili |
| 5,769,832 A | 6/1998 | Hasse et al. |
| 6,229,062 B1 | 5/2001 | Mandell et al. |
| 6,362,374 B1 | 3/2002 | Forester et al. |
| 6,376,741 B1 | 4/2002 | Guarracino et al. |
| 6,379,658 B1 | 4/2002 | Marano et al. |
| 6,403,075 B1 | 6/2002 | Costa et al. |
| 6,610,648 B2 | 8/2003 | McGee et al. |
| 7,585,833 B2 | 9/2009 | Fadel et al. |
| 8,007,771 B2 | 8/2011 | Ramji et al. |
| 8,865,192 B2 | 10/2014 | Swaine et al. |
| 9,061,965 B2 | 6/2015 | Pluyter et al. |
| 9,126,890 B2 | 9/2015 | Pluyter et al. |

(Continued)

FOREIGN PATENT DOCUMENTS

DE 19837539 A1 2/2000
EP 2272491 A1 1/2011

(Continued)

OTHER PUBLICATIONS

EPO Examination Report dated Mar. 16, 2016.
(Continued)

Primary Examiner — Robert A Wax
Assistant Examiner — Quanglong N Truong
(74) Attorney, Agent, or Firm — Martin Zhang; Xufan Tseng; Elizabeth M. Stover

(57) ABSTRACT

A malodor counteracting composition contains a malodor counteractant that is capable of neutralizing a malodor and a stabilizer that is capable of decreasing or preventing self-polymerization of the malodor counteractant. The malodor counteractant has a backbone and one or more reactive end groups that are covalently attached to the backbone, the backbone has a molecular weight of 100 to 50,000 Daltons, and the one or more reactive end groups each have an $\alpha,\beta$-unsaturated carbonyl group. Also disclosed are consumer, industrial or textile products containing the malodor counteracting composition and methods of neutralizing malodor using the composition.

20 Claims, No Drawings

(56) References Cited

U.S. PATENT DOCUMENTS

| | | |
|---|---|---|
| 2002/0058017 A1 | 5/2002 | Tajima et al. |
| 2004/0024876 A1 | 2/2004 | Ito et al. |
| 2004/0082707 A1 | 4/2004 | Pears |
| 2004/0209269 A1 | 10/2004 | Dugas et al. |
| 2006/0022825 A1 | 2/2006 | Carrender |
| 2008/0242721 A1 | 10/2008 | Selifonov |
| 2010/0011188 A1 | 1/2010 | Eddy et al. |
| 2010/0179262 A1 | 7/2010 | Dams et al. |
| 2010/0247825 A1 | 9/2010 | Wood et al. |
| 2011/0070181 A1 | 3/2011 | Williams et al. |
| 2012/0101187 A1 | 4/2012 | Kuo et al. |
| 2012/0294821 A1 | 11/2012 | Pluyter et al. |
| 2015/0336877 A1 | 11/2015 | Pluyter et al. |

FOREIGN PATENT DOCUMENTS

| | | |
|---|---|---|
| EP | 2412677 A1 | 2/2012 |
| GB | 735693 | 7/1951 |
| JP | 2006176433 | 7/2006 |
| WO | 2002051788 A1 | 2/2000 |
| WO | 2001036362 A2 | 5/2001 |
| WO | 2005021051 A1 | 3/2005 |
| WO | 2006076821 A1 | 7/2006 |
| WO | 2007012586 A1 | 2/2007 |
| WO | 2008005548 A2 | 1/2008 |
| WO | 2011034997 A2 | 3/2011 |

OTHER PUBLICATIONS

Chinese 2nd Office Action dated Jul. 15, 2015 (and its English translation).
Chinese 1st Office Action dated Nov. 3, 2014.
European Search Opinion dated Jan. 28, 2013.
European Search Report dated Sep. 19, 2012.
Lee, S.G., et al., "Presence of D-Alanine in anEndopeptidase from *Streptococcus pyogenes*", The Journal of Biological Chemistry, vol. 278, No. 47, pp. 46649-46653, (Nov. 21, 2003).
Wabnitz, T.C., et al., "A General Brønsted Acid-Catalyzed Hetero-Michael Addition of Nitrogen, Oxygen, and Sulfer Nucleophiles", Organic Letters, vol. 5, No. 12, pp. 2141-2144, (2003).
Sutherland, I. W., "Structural Studies on Colanic Acid, the Common Exopolysaccharide Found in the Enterobacteriaceae, by Partial Acid Hydrolysis—Oligosaccharides from Colanic Acid", Biochem. J., vol. 115, pp. 935-945,(1969).
Zeng, X-N., et al., "Analysis of Characteristic Odors from Human Male Axillae", Journal of Chemical Ecology, vol. 17, No. 7, pp. 1469-1492, (1991).
Sun, G., et al., "Benzaldehyde-functionalized Polymer Vesicles", ACS Nano, vol. 3, No. 3, pp. 673-681, (Mar. 24, 2009).
Office Communication dated Jun. 25, 2012 from U.S. Appl. No. 13/277,288, filed Oct. 20, 2011.
Akiyama, Y., et al., "Synthesis of Heterotelechelic Poly(ethylene glycol) Derivatives Having α-Benzaldehyde and ω-Pyridyl Disulfide Groups by Ring Opening Polymerization of Ethylene Oxide Using 4-(Diethoxymethyl)benzyl Alkoxide as a Novel Initiator", Bioconjugate Chem., vol. 15, pp. 424-427, (2004).
Definition of "polyol" from Dictionary.com, downloaded Oct. 17, 2014, from the site: "http://dictionary.reference.com/browse/polyol".
Bianchi, E., et al., "Free Radical Grafting onto Cellulose in Homogeneous Conditions. 2. Modified Cellulose-methyl methacrylate system", Carbohydrate Polymers, vol. 41, pp. 47-53, (2000).
Marsano, E., et al., "Cellulose Methacrylate: Synthesis and Liquid Crystalline Behaviour of Solutions and Gels", Polymer, vol. 39, No. 18, pp. 4289-4294, (1998).
Heggli, M., et al., "Michael-Type Addition as a Tool for Surface Functionalization", Bioconjugate Chem., vol. 14, pp. 967-973, (2003).
Google Scholar Search Results for peg acrylate scavenger downloaded from this site Dec. 22, 2012: http://scholar.google.com/scholar?q=peg+acrylate+scavenger&hl=en&as_sdt=)52C$7 . . . .
Kahovec Jaroslav, "Aldehyde Functionalization of Styrene Polymers", Polymer Bulletin, vol. 4, No. 12, (Jun. 1, 1981), pp. 731-733.

MALODOR COUNTERACTING COMPOSITIONS

BACKGROUND OF THE INVENTION

Malodors typically come from amines, thiols, sulfides, short chain aliphatic and olefinic acids, e.g. fatty acids. Those chemicals are found in sweat, household, and environmental malodors. Common malodors include secondary aromatic amines such as indole and skatole, and thiols (e.g., methanethiol) found in toilet and animal odors; heterocyclic amines such as piperidine and morpholine found in urine; and tertiary amines such as pyridine and triethyl amine found in kitchen and garbage odors; and short chain fatty acids, such as 3-methyl-3-hydroxyhexanoic acid, 3-methylhexanoic acid or 3-methyl-2-hexenoic acid, found in axillary malodors. See Xiao-Nong Zeng, et al. (1991) *J. Chem. Ecol.* 17, 1469-92.

Malodor counteractants or masking agents have been used to neutralize the offensive odors. For example, sulfhydryl reactants, such as diethyl fumarate, di-n-butyl maleate and N-ethylmaleimide are disclosed in U.S. Pat. No. 5,601,809 as compounds that are effective against axillary malodor. Further, the use of certain aromatic unsaturated carboxylic acid esters in combination with alkyl fumarates as malodor counteractants is disclosed in WO 2002/051788. U.S. Pat. No. 6,403,075 addresses fragrance materials with a phenyl ring moiety as ammonia masking agents. Similarly, US 2002/0058017 describes cis-3-hexenol to mask ammonia. Moreover, U.S. Pat. No. 7,585,833 describes methods for formulating fragrances to mask malodor present in products containing ammonia and substituted amines. See also U.S. Pat. No. 6,379,658, U.S. Pat. No. 6,376,741, U.S. Pat. No. 5,769,832 and U.S. Pat. No. 5,037,412.

Most known counteractants are highly volatile. They are not capable of controlling malodors for an extended period of time.

There is a need for counteractants that are effective against malodors and last for a long time.

SUMMARY OF THE INVENTION

This invention features malodor counteractive compositions that are stable for a prolonged period of time and effective for counteracting thiol- or amine-based malodors.

One aspect of this invention relates to a malodor counteracting composition containing (i) a malodor counteractant that is capable of neutralizing a malodor and (ii) a stabilizer that is capable of decreasing or preventing self-polymerization of the malodor counteractant.

The malodor counteractant has a backbone and one or more reactive end groups that are covalently attached to the backbone, the backbone has a molecular weight of 100 to 10,000,000 (e.g., 100 to 50,000 Daltons and 120 to 5,000 Daltons), and the one or more reactive end groups each have an α,β-unsaturated carbonyl group. The backbone can be a polymer, an oligomer, a surfactant, or a combination thereof, and α,β-unsaturated carbonyl group is an ionone moiety, an irone moiety, a damascone moiety, an acryloxy moiety, a methacryloxy moiety, an acrylamide moiety, a methacrylamide moiety, or a crotonate moiety. Exemplary polymers are polyols, polysaccharides, polyamines, polyethylene imines, polyacrylates, and polyalkylene oxides. Suitable oligomers include oligosaccharides and oligomeric alkanes. The surfactant can be a poloxamine or alkoxylated fatty acid.

Examples of a stabilizer include, but are not limited to, pentaerythrityl tetra-di-t-butyl hydroxyhydrocinnamate, methyl-3-(3,5-di-tert-butyl-4-hydroxyphenyl)propanoate, hydroquinone monomethyl ether, phenothiazine, butylated hydroxy toluene, butylated hydroxy anisole, 1,7-bis(4-hydroxyphenyl)-1,4,6-heptatrien-3-one, (4aR,10aS)-5,6-dihydroxy-1,1-dimethyl-7-propan-2-yl-2,3,4,9,10,10a-hexahydrophenanthrene-4a-carboxylic acid, (1E,6E)-1,7-bis(4-hydroxy-3-methoxyphenyl)-1,6-heptadiene-3,5-dione, (1E,6E)-1-(4-hydroxy-3-methoxyphenyl)-7-(4-hydroxyphenyl)hepta-1,6-diene-3,5-dione, (E)-3-(4-hydroxy-3-methoxyphenyl)prop-2-enoic acid, 4-(2-hydroxyethyl)-1,2-benzenediol, 4,4'-(2,3-dimethylbutane-1,4-diyl)dibenzene-1,2-diol, 2-(4-hydroxyphenyl)ethyl (3S,4E)-4-formyl-3-(2-oxoethyl)hex-4-enoate, 1-(4-hydroxy-3-methoxyphenyl)decan-3-one, 3,4-dihydroxybenzoic acid, a tocopherol, ascorbic acid, retinol, retinal, retinoic acid, retinyl acetate, retinyl palmitate, alpha-carotene, beta-carotene, gamma-carotene, lutein, lycopene, glutathione, (2"R")-2-oxy]-3-(3,4-dihydroxyphenyl)propanoic acid, 3,4-methylenedioxyphenol, 3,4,5-trihydroxy-1,8-bis[(2R,3R)-3,5,7-trihydroxy-2-chromanyl]-6-benzo[7]annulenone, theaflavin-3,3'-digallate, 4-(2-hydroxyethyl)phenol, tannic acid, ellagic acid, catechin, epicatechin pyrocatechol, resorcinol, pyrogallol, phloroglucinol, and any combination thereof.

The above malodor counteracting composition optionally contains an end solvent selected from the group consisting of ethanol, methanol, ethyl acetate, propylene glycol, diphenyl phthalate, dipropylene glycol, tripropylene glycol, water, ethylene glycol, diethyl phthalate, 1-methoxy-2-propanol, 2-methoxy-1-methylethyl acetate, tripropylene glycol methyl ether, dipropylene glycol methyl ether, dipropylene glycol n-butyl ether, dipropylene glycol methyl ether acetate, triacetin, 1-methyl-4-isopropylidene-1-cyclohexene, 2-(4-methyl-1-cyclohex-3-enyl)propan-2-ol, and a combination thereof.

In any of the malodor counteracting compositions described above, the acrylic acid or methacrylic acid content can be at a level of 2000 ppm or less (e.g., 1000 ppm or less, 500 ppm or less, and 300 ppm or less). These acids are undesirable side products during the preparation of the malodor counteractant or when the malodor counteractant is decomposed.

A subset of the malodor counteracting compositions contains a malodor counteractant having Formula I:

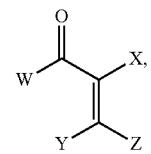

In this formula, each of W, X, Y, and Z, independently, is H, halo, nitro, cyano, $C_1$-$C_{10}$ alkyl, $C_1$-$C_{10}$ alkoxy, $C_2$-$C_{10}$ alkenyl, $C_2$-$C_{10}$ alkynyl, $C_3$-$C_{10}$ cycloalkyl, $C_1$-$C_{10}$ heterocycloalkyl, $C_1$-$C_{10}$ alkylamino, $C_1$-$C_{20}$ dialkylamino, or -Q-P, provided that at least one of W, X, Y, and Z is -Q-P. P can be a polymer, oligomer, or surfactant moiety and Q can be a bond, O, S, $NR^1$, or $CR^2R^3$, in which each of $R^1$, $R^2$, and $R^3$, independently, is H, halo, OH, nitro, cyano, $C_1$-$C_{10}$ alkyl, $C_1$-$C_{10}$ alkoxy, $C_2$-$C_{10}$ alkenyl, $C_2$-$C_{10}$ alkynyl, $C_3$-$C_{10}$ cycloalkyl, $C_1$-$C_{10}$ heterocycloalkyl, $C_1$-$C_{10}$ alkylamino, or $C_1$-$C_{20}$ dialkylamino; $R^1$ together with the nitrogen atom to which it attaches is a $C_1$-$C_{10}$ heterocycloalkyl or heteroaryl; or $R^2$ and $R^3$, together with the carbon atom to which they are attached, are $C_3$-$C_{10}$ cycloalkyl, $C_1$-$C_{10}$ heterocycloalkyl, aryl, or heteroaryl. Preferably, Q is NH; P, having an average molecular weight of 1,000 to 10,000 (e.g., 200 to 5000 Daltons) and the molecular weight distribution ranging from 100 to 50,000 Daltons, is a poly(ethylene oxide), poly(propylene oxide), or poly(ethylene oxide-co-propylene oxide). Each of X, Y, and Z, independently, can be H or methyl.

Another aspect of this invention relates to a method of neutralizing a malodor a consumer, industrial or textile product, the method comprising the step of: (i) providing any one of the malodor counteracting compositions described above, and (ii) adding the malodor counteracting composition to a consumer, industrial or textile product so that the product is capable of neutralizing a malodor by using the malodor counteractant to react with or absorbing the malodor. The consumer, industrial, or textile product can be a home care product, a fabric care product, or a personal care product.

The details of one or more embodiments of the invention are set forth in the description below. Other features, objects, and advantages of the invention will be apparent from the description and the claims.

DETAILED DESCRIPTION OF THE INVENTION

The present invention provides malodor counteracting compositions each containing a malodor counteractant and a stabilizer.

The malodor counteractants can be soluble or insoluble in water. Preferably, they are insoluble.

The malodor counteractant has a backbone and one or more reactive end groups that are covalently attached to the backbone.

The backbone can be a polymer, an oligomer, a surfactant, or a combination thereof. The malodor counteractants containing this backbone each have a low vapor pressure such that they can be added in significant quantities to products without impacting the olfactory character of the products other than neutralizing malodors. Vapor pressure)(P° is the pressure of a vapor of a compound in equilibrium with its pure condensed phase (solid or liquid) at a given temperature in a closed system. It can be measured as in pascals (Pa). One pa is one newton per square meter ($N·^{m-2}$ or $kg·^{m-1·s-2}$). Vapor pressures depend on the temperature and vary with different compounds due to differences in molecule-molecule interactions. For example, vapor pressure at 25° C. of n-alkanes is a function of chain length, wherein larger n-alkane molecules have lower P° due to greater polarizability and increased strength of London Dispersion intermolecular forces. The vapor pressure of a compound can be determined by conventional methods known to those of skill in the art. In particular embodiments, counteractants useful in this invention each have a vapor pressure at 25° C. of less than about 200 Pa (i.e., about 1.5 mmHg), less than about 100 Pa (i.e., about 0.75 mmHg), less than about 50 Pa (i.e., about 0.375 mmHg), less than about 20 Pa (i.e., about 0.15 mmHg), less than about 10 Pa (i.e., about 0.075 mmHg), less than about 1 Pa (i.e., about 0.0075 mmHg), or less than about 0.1 Pa (i.e., about 0.00075 mmHg).

Useful as a backbone, a polymer is a molecule composed of a plurality of (e.g., 10 or more) repeating monomer units. The term "polymer" as used herein includes homopolymers, which are formed from a single type of monomer, and copolymers, which are formed from two or more different monomers. In copolymers, the monomers is distributed randomly (random copolymer), in alternating fashion (alternating copolymers), or in blocks (block copolymer). Suitable polymers can have about 10 to about 200 (e.g., about 10 to about 100, about 10 to about 50, and about 10 to about 25) monomer units, with average molecular weights that range from about 120 Daltons to about 1,000,000 Daltons, or from about 135 Daltons to about 120,000 Daltons. Preferred polymers are those having about 10 to about 25 monomer units, with average molecular weights that range from about 135 Daltons to about 25,000 Daltons. Suitable polymers include polyols (e.g., polyvinyl alcohols and its copolymers), polysaccharides (e.g., maltodextrin), polyamines (e.g., polyvinyl amines and its copolymers), polyimines (e.g., polyethylene imine), polyacrylates with OH groups, polyalkylene oxides with OH or $NH_2$ end groups (e.g., polyethylene glycol, "PEG") and block and random copolymers thereof.

Oligomers are also useful as backbones. The term "oligomer" as used herein refers to a molecule having 1 to 9 (e.g., 2 to 9) monomer units. They generally have a molecular weight of 5,000 Daltons or lower (e.g., about 100 to about 5,000 Daltons and about 120 to 2,500 Daltons). In contrast to a polymer, which can contain a large number of monomers, an oligomer is composed of a few monomer units. In this respect, oligomers include dimers (formed of two monomers), trimers (formed of three monomers), tetramers (formed of two monomers), and the like. Exemplary oligomers are oligosaccharides and oligomeric alkanes (e.g., pentanes, butanes, or hexane).

The term "polymer" or "oligomer" used herein also includes that portion of the polymer or oligomer which is a continuous chain comprising the bonds formed between monomers upon polymerization. The composition of the polymer or oligomer can be described in terms of the identity of the monomers from which it is formed without regard to the composition of branches, or side chains, of the polymer or oligomer backbone.

In particular embodiments, the malodor counteractant of the present invention is a small molecule with no-to-low vapor pressure attached to one or more α,β-unsaturated carbonyl groups.

Solid surfaces can also be used as backbones. Examples include silica surfaces (e.g., a synthetic amorphous silica surface such as SYLOID), clay or other solid mineral materials with an appropriate functional group to attaching the α,β-unsaturated carbonyl moiety. In some embodiments, the solid surface is the surface of a delivery system such as a nanoparticle, microparticle, nanocapsule, or microcapsule, containing one or more α,β-unsaturated carbonyl moieties as described herein.

Also useful as backbones, surfactants are compounds that lower the surface tension of a liquid, the interfacial tension between two liquids, or that between a liquid and a solid. Surfactants can act as detergents, wetting agents, emulsifiers, foaming agents, and dispersants. They are usually organic compounds that are amphiphilic. Examples include poloxamines, alkoxylated fatty acids, PLURONIC surfactants (based on ethylene oxide, propylene oxide and/or butylenes oxide as di- or tri-block copolymers) and TETRONIC surfactants (poloxamine or block copolymers based on ethylene oxide and propylene oxide with a vapor pressure of <0.1 mmHg at 25° C.) such as TETRONIC 901, TETRONIC 701, TETRONIC 90R4, and TETRONIC 904, and LUTENSOL AO nonionic surfactants (unbranched $C_{13}$-$C_{15}$ oxo alcohol) including LUTENSOL AO3, LUTENSOL AO4, LUTENSOL AO5, and LUTENSOL AO7.

The reactive end groups each have an α,β-unsaturated carbonyl moiety. According to particular embodiments, the α,β-unsaturated carbonyl moiety is a radical of an odorant or fragrance such as an ionone, irone, damascone or a structurally related molecule. Examples of this class of molecules include α-damascone, β-damascone, δ-damascone, isodamascone, γ-methylionone, dynascone, α-irone, dihydroirone, α-ionone, β-ionone and trimethylcyclohexyl)-pent-1-en-3-one. In another embodiment, the α,β-unsaturated carbonyl moiety is a crotonate such as geranyl crotonate, ethyl crotonate, methyl crotonate, benzyl crotonate and the like. In yet another embodiment, the α,β-unsaturated carbonyl moiety is an acrylate, methacrylate (e.g., glycidyl methacrylate), acrylamide, or methacrylamide group. The acrylate or methacrylate group can be incorporated into compounds of Formula I via either the carboxyl group or α,β-unsaturated C=C group while the acrylamide or methacrylamide group can be incorporated into compounds of Formula I via either the amide group or α,β-unsaturated C=C group. In particular embodiments, the α,β-unsaturated carbonyl moiety is e.g., acetic acid 2,5-dimethyl-bicyclo[3.2.1]oct-2-en-3-yl ester; acetic acid 1,4-dimethyl-bicyclo[3.2.1]oct-2-en-3-yl ester; 4-allyl-1,4-dimethyl-bicyclo[3.2.1]octan-3-one or a derivative thereof.

Exemplary α,β-unsaturated carbonyl moieties are shown by chemical structures as follows:

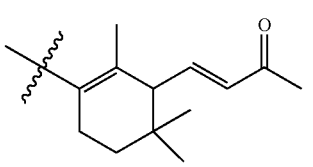

alpha-ionone

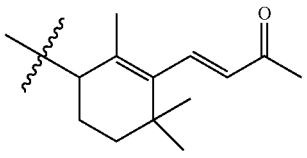

beta-ionone

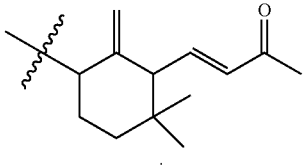

gamma-ionone

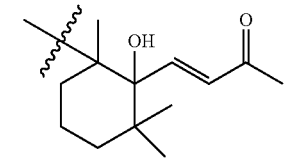

hydroxy-alpha-ionone

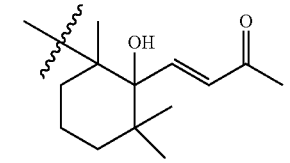

hydroxy-beta-ionone

-continued

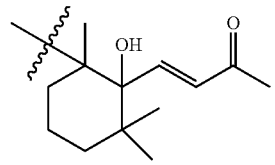

hydroxy-gamma-ionone

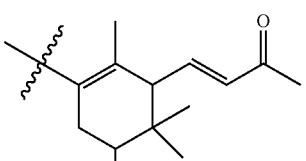

alpha-irone

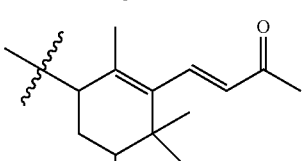

beta-irone

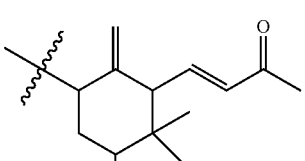

gamma-irone

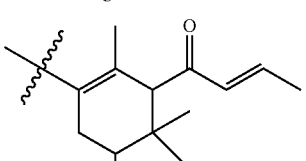

alpha-damascone

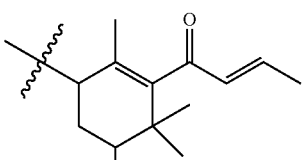

beta-damascone

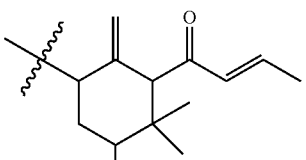

gamma-damascone

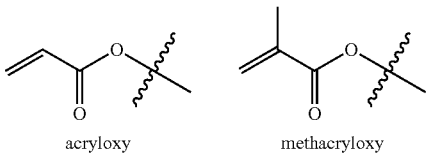

acryloxy                    methacryloxy

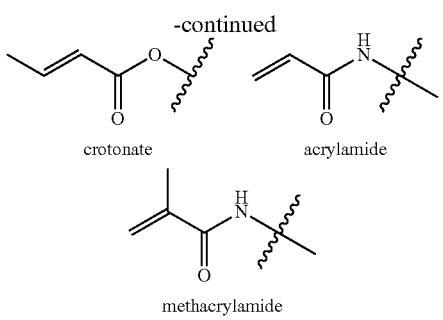

crotonate    acrylamide methacrylamide

In the scheme above, a wavy line indicates where the bond connects to the backbone of the malodor counteractant useful in this invention.

Without wishing to be bound by any theory, the α,β-unsaturated carbonyl groups can bind to or react with thiol- and amine-based malodors (e.g., through Michael addition of thiol/amine groups to the α,β-unsaturated carbonyl groups) thereby effectively immobilizing these malodors or reducing their concentration in consumer, industrial or textile products.

The α,β-unsaturated carbonyl moieties typically attach through a covalent bond to a backbone to form malodor counteractants useful in this invention. Given that the α,β-unsaturated carbonyl moiety is covalently attached, this moiety is not released before or during use in a consumer, industrial or textile product, e.g., the instant compound is not a pro-fragrances.

As an illustration, certain malodor counteractants can be prepared by acrylation or acrylamidation of a polymer, an oligomer, a solid surface, a surfactant or a low volatile organic or inorganic compound. Other malodor counteractants can be prepared using known preparation procedures. See Montalbetti et al., Tetrahedron, 61, 10827-53 (2005).

Typically, acrylation is achieved by a reaction between acryloyl chloride ($CH_2$=CH—COCl) or methacryloyl chloride ($CH_2$=C($CH_3$)—COCl) and a hydroxyl group on a backbone to form an acrylate or methacrylate. Similarly, an acrylamide/methacrylamide can be prepared by reactions between acryloyl chloride/methacryloyl chloride and a primary or secondary amine group on a backbone.

The reactions are carried out in a reaction solvent that is compatible (i.e., not reacting) with acryloyl chloride and methacryloyl chloride. Suitable reaction solvents include methylene chloride, dimethyl sulfoxide ("DMSO"), dimethylformamide ("DMF"), tetrahydrofuran ("THF"), dioxane, chloroform, toluene, and the like.

Due to their toxicity, these reaction solvents need to be removed from the malodor counteracting composition of this invention. In some embodiment, a nonsolvent is added to the reaction mixture to precipitate the malodor counteractant as a solid. The solid malodor counteractant is then collected by filtration. A nonsolvent is a liquid in which the malodor counteractant has a low solubility (e.g., a solubility of 100 mg/mL or less, 10 mg/mL or less, and 1 mg/mL or less). Exemplary nonsolvents include acetone, water, and ethanol. In some embodiments, the reaction solvent is removed by evaporation. In other embodiments, the reaction solvent is removed by solvent exchange with an end solvent, which is added to a solution of the malodor counteractant in the reaction solvent. Typically, an end solvent can be added to the reaction mixture. Subsequent co-distillation removes both the reaction solvent and the end solvent. By using a large amount of the end solvent or refilling the reaction mixture with the end solvent, the reaction solvent is replaced with the end solvent and reduced in the resultant malodor counteracting composition to a level of 2 wt % or less (e.g., 1 wt % or less, 0.5 wt % or less, 0.2 wt % or less, 0.1 wt % or less, and 0.05 wt % or less). To reduce the reaction solvent to a desired level, a skilled person in the art can choose an end solvent based on the boiling points of both the end and reaction solvents. The amount of end solvent can also be readily determined without undue experimentation.

After evaporation, most of the reaction solvent is removed to obtain the malodor counteractive composition of this invention containing the malodor counteractant dissolved or suspended in the end solvent. Suitable end solvents include ethanol, methanol, ethyl acetate, propylene glycol, diphenyl phthalate, dipropylene glycol, tripropylene glycol, water, ethylene glycol, diethyl phthalate, 1-methoxy-2-propanol, 2-methoxy-1-methylethyl acetate, tripropylene glycol methyl ether, dipropylene glycol methyl ether, dipropylene glycol n-butyl ether, dipropylene glycol methyl ether acetate, triacetin, 1-methyl-4-isopropylidene-1-cyclohexene, 2-(4-methyl-1-cyclohex-3-enyl)propan-2-ol, and combinations thereof.

During the co-distillation, a stabilizer can be added to a reaction mixture along with an end solvent. It was unexpectedly found that the stabilizer maintained the malodor counteracting activity.

Malodor counteractants containing an α,β-unsaturated carbonyl group can react with each other (e.g., by self-condensation) to decrease its malodor neutralizing activity, especially during the removal of the reaction solvent by evaporation or solvent exchange. Without a stabilizer, some malodor counteractants of this invention can be turned into a gel and render them useless for malodor counteracting. In order to keep the counteracting activity, it is necessary to avoid self-condensation and other reactions that decrease the malodor neutralizing activity.

It has been unexpectedly found that certain stabilizers can prevent malodor counteractants from reacting with each other and at the same time keep their malodor neutralizing activity. The stabilizers can also prolong the shelf lives of the counteractants.

Exemplary stabilizers include pentaerythrityl tetra-di-t-butyl hydroxyhydrocinnamate, methyl-3-(3,5-di-tert-butyl-4-hydroxyphenyl)propanoate, hydroquinone monomethyl ether, phenothiazine, butylated hydroxy toluene, butylated hydroxy anisole, 1,7-bis(4-hydroxyphenyl)-1,4,6-heptatrien-3-one, (4aR,10aS)-5,6-dihydroxy-1,1-dimethyl-7-propan-2-yl-2,3,4,9,10,10a-hexahydrophenanthrene-4a-carboxylic acid, (1E,6E)-1,7-bis(4-hydroxy-3-methoxyphenyl)-1,6-heptadiene-3,5-dione, (1E,6E)-1-(4-hydroxy-3-methoxyphenyl)-7-(4-hydroxyphenyl)hepta-1,6-diene-3,5-dione, (E)-3-(4-hydroxy-3-methoxy-phenyl)prop-2-enoic acid, 4-(2-hydroxyethyl)-1,2-benzenediol, 4,4'-(2,3-dimethylbutane-1,4-diyl)dibenzene-1,2-diol, 2-(4-hydroxyphenyl)ethyl (3S,4E)-4-formyl-3-(2-oxoethyl)hex-4-enoate, 1-(4-hydroxy-3-methoxy-phenyl)decan-3-one, 3,4-dihydroxybenzoic acid, a tocopherol, ascorbic acid, retinol, retinal, retinoic acid, retinyl acetate, retinyl palmitate, alpha-carotene, beta-carotene, gamma-carotene, lutein, lycopene, glutathione, (2"R")-2-oxy]-3-(3,4-dihydroxyphenyl)propanoic acid, 3,4-methylenedioxyphenol, 3,4,5-trihydroxy-1,8-bis[(2R,3R)-3,5,7-trihydroxy-2-chromanyl]-6-benzo[7]annulenone, theaflavin-3,3'-digallate, 4-(2-hydroxyethyl)phenol, tannic acid, ellagic acid, catechin, epicatechin pyrocatechol, resorcinol, pyrogallol, phloroglucinol, and any combination thereof. More stabilizers can be found in Evgeny T. Denisov et al., Handbook of Antioxidants: Bond Dissociation Energies, Rate Constants, Activation Energies and Enthalpies of Reactions, CRC Press (November, 1999).

The content of the stabilizer in the composition can be 0.001 wt % to 1 wt % (preferably 0.005 wt % to 0.5 wt %, and more preferably 0.01 wt % to 0.1 wt %). Suitable molar ratios between the stabilizer and the counteractant are 10,000:1 to 10:1 (preferably 1000:1 to 50:1, and more preferably 600:1 to 100:1). The malodor composition containing the stabilizer is stable at 25° C. for at least 1 day (e.g., at least 2 days, 4 days, 1 week, 2 weeks, 1 month, and 6 months). A composition is stable if the composition maintained 50% or more (e.g., 60% or more and 80% or more) of its original malodor counteracting activity or 80% (e.g., 60% or more and 80% or more) of the reactive end groups on the malodor counteractant remain intact.

In particular embodiments, a malodor counteractant of this invention is a compound of Formula I:

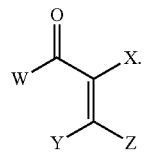

I

In this formula, each of W, X, Y, and Z, independently, is H, halo, nitro, cyano, $C_1$-$C_{10}$ alkyl, $C_1$-$C_{10}$ alkoxy, $C_2$-$C_{10}$ alkenyl, $C_2$-$C_{10}$ alkynyl, $C_3$-$C_{10}$ cycloalkyl, $C_1$-$C_{10}$ heterocycloalkyl, $C_1$-$C_{10}$ alkylamino, $C_1$-$C_{20}$ dialkylamino, or -Q-P, provided that at least one of W, X, Y, and Z is -Q-P, P being a polymer, oligomer, or surfactant moiety, Q being a bond, O, S, $NR^1$, or $CR^2R^3$, in which each of $R^1$, $R^2$, and $R^3$, independently, is H, halo, OH, nitro, cyano, $C_1$-$C_{10}$ alkyl, $C_1$-$C_{10}$ alkoxy, $C_2$-$C_{10}$ alkenyl, $C_2$-$C_{10}$ alkynyl, $C_3$-$C_{10}$ cycloalkyl, $C_1$-$C_{10}$ heterocycloalkyl, $C_1$-$C_{10}$ alkylamino, or $C_1$-$C_{20}$ dialkylamino; R1 together with the nitrogen atom to which it attaches is a $C_1$-$C_{10}$ heterocycloalkyl or heteroaryl; or $R^2$ and $R^3$, together with the carbon atom to which they are attached, are $C_3$-$C_{10}$ cycloalkyl, $C_1$-$C_{10}$ heterocycloalkyl, aryl, or heteroaryl.

Specific examples of malodor counteractant compounds of the invention include, but are not limited to, the following compounds.

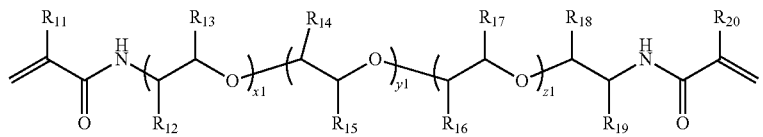

y1 being 1 to 50 and x1+z1 being 0 to 100
each of $R_{11}$, $R_{12}$, $R_{13}$, $R_{14}$, $R_{15}$, $R_{16}$, $R_{17}$, $R_{18}$, $R_{19}$, and $R_{20}$, independently,
being H, $CH_3$, or $CH_2CH_3$
preferably, y1 being 1 to 40 and x1+z1 being 10 to 70
more preferably, y1 being 3 to 20 and x1+z1 being 20 to 50

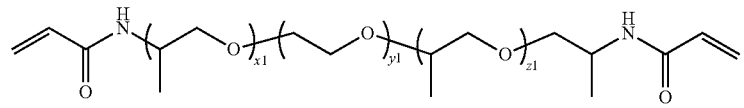

y1 being 1 to 50 and x1+z1 being 0 to 100
preferably, y1 being 1 to 40 and x1+z1 being 10 to 70
more preferably, y1 being 3 to 20 and x1+z1 being 20 to 50

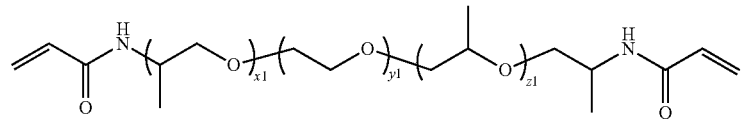

y1 being 1 to 50 and x1+z1 being 0 to 100
preferably, y1 being 1 to 40 and x1+z1 being 10 to 70
more preferably, y1 being 3 to 20 and x1+z1 being 20 to 50

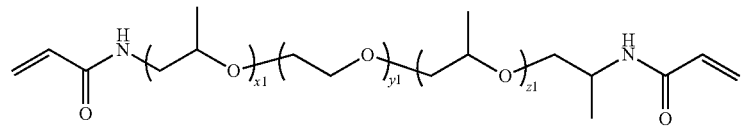

y1 being 1 to 50 and x1+z1 being 0 to 100
preferably, y1 being 1 to 40 and x1+z1 being 10 to 70
more preferably, y1 being 3 to 20 and x1+z1 being 20 to 50

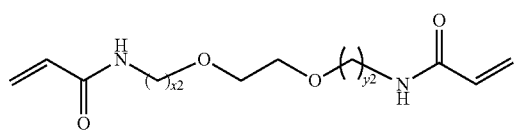

y1 being 1 to 50 and x1+z1 being 0 to 100
preferably, y1 being 1 to 40 and x1+z1 being 10 to 70
more preferably, y1 being 3 to 20 and x1+z1 being 20 to 50

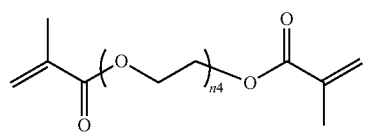

x2 being 0 to 50 and y2 being 0 to 50
preferably, x2 being 2 to 25 and y2 being 2 to 25
more preferably, x2 being 2 to 12 and y2 being 2 to 12

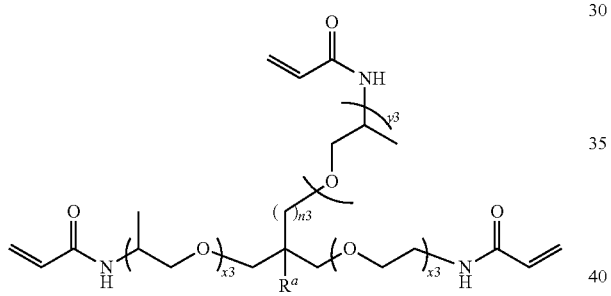

x3+y3+z3 being 1 to 200, n3 being 0 to 10, and $R^a$ being H, $CH_3$, or $C_2H_5$
preferably, x3+y3+z3 being 20 to 150, n3 being 0 to 6
more preferably, x3+y3+z3 being 50 to 120, n3 being 0 to 4

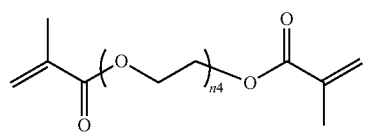

n4 being 1 to 400
preferably, n4 being 1 to 100
more preferably, n4 being 10 to 100

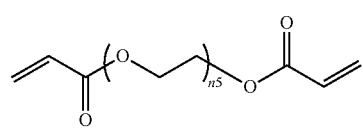

n5 being 1 to 400
preferably, n5 being 1 to 100
more preferably, n5 being 10 to 100

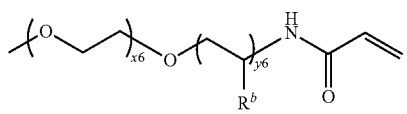

x6 being 1-80, y6 being 1 to 80, and $R^b$ being H, $CH_3$, or $CH_2CH_3$
preferably, x6 being 4 to 80, y6 being 4 to 80
more preferably, x6 being 4 to 50, y6 being 4 to 50

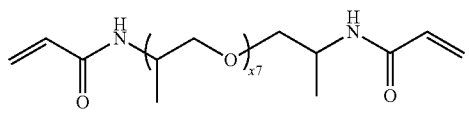

x7 being 1 to 80
preferably, x7 being 5 to 80
more preferably, x7 being 10 to 50

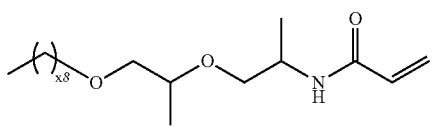

x8 being 4 to 24
preferably, x8 being 4 to 18
more preferably, x8 being 4 to 14

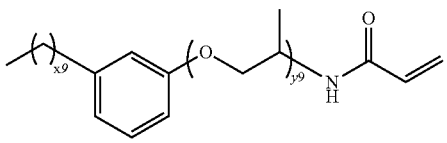

x9 being 1 to 18 and y9 being 5 to 25
preferably, x9 being 4 to 18 and y9 being 5 to 20
more preferably, x9 being 4 to 10 and y9 being 5 to 15

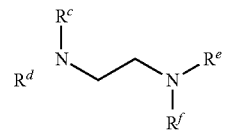

each of $R^c$, $R^d$, $R^e$, and $R^f$, independently, being

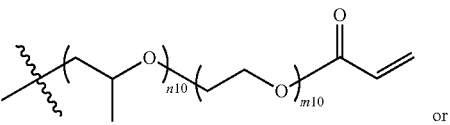

or

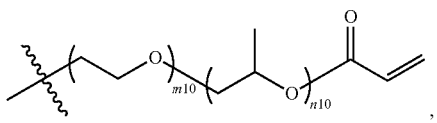

in which each of m10 and n10, independently, is 1 to 80
preferably, each of m10 and n10, independently, is 4 to 80
more preferably, each of m10 and n10, independently, is 4 to 40

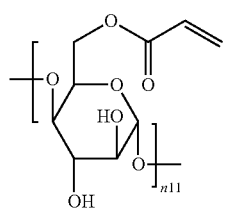

n11 being 10 to 100,000
preferably, n11 being 10 to 10,000
more preferably, n11 being 10 to 1000

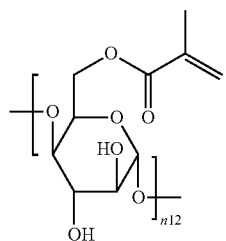

n12 being 10 to 100,000
preferably, n12 being 10 to 10,000
more preferably, n12 being 10 to 1000

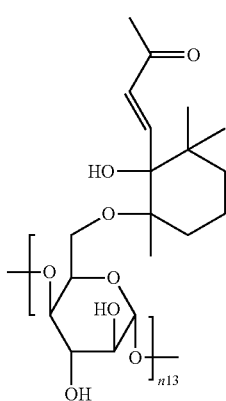

n13 being 10 to 100,000
preferably, n13 being 10 to 10,000
more preferably, n13 being 10 to 1000

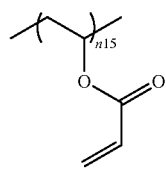

n14 being 1 to 80 and m14 being 4 to 24
preferably, n14 being 1 to 60 and m14 being 4 to 18
more preferably, n14 being 1 to 40 and m14 being 4 to 12

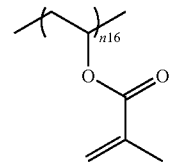

n15 being 300 to 40,000
preferably, n15 being 300 to 20,000
more preferably, n15 being 300 to 10,000

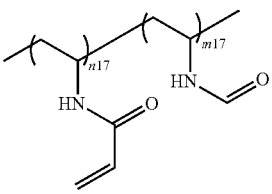

n16 being 300 to 40,000
preferably, n16 being 300 to 20,000
more preferably, n16 being 300 to 10,000

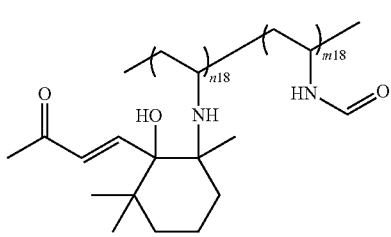

each of m17 and n17, independently, being 300 to 40,000
preferably, each of m17 and n17, independently, being 300 to 20,000
more preferably, each of m17 and n17, independently, being 300 to 10,000 each of m18 and n18, independently, being 300 to 40,000 preferably, each of m18 and n18, independently, being 300 to 20,000 more preferably, each of m18 and n18, independently, being 300 to 10,000

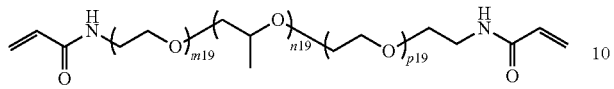

each of m19, n19, and p19, independently, being 1 to 100 preferably, each of m19, n19, and p19, independently, being 4 to 80 more preferably, each of m19, n19, and p19, independently, being 4 to 40

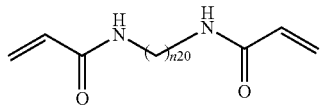

n20 being 6 to 24 preferably, n20 being 6 to 18 more preferably, n20 being 6 to 14

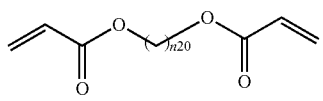

m20 being 6 to 24 preferably, m20 being 6 to 18 more preferably, m20 being 6 to 14

n21 being 10 to 50 (preferably, 10 to 40 and more preferably, 10 to 25)

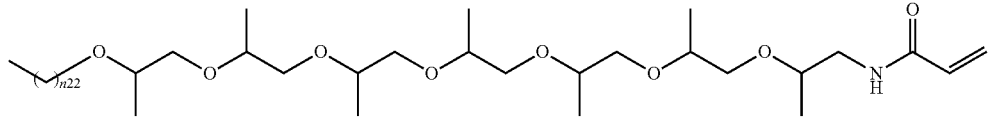

n22 being 10 to 50 (e.g., 10 to 40 and 10 to 25)

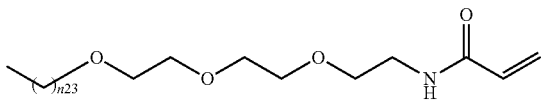

n23 being 10 to 50 (e.g., 10 to 40 and 10 to 25)

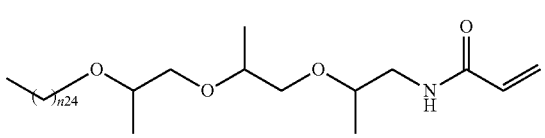

n24 being 10 to 50 (e.g., 10 to 40 and 10 to 25)

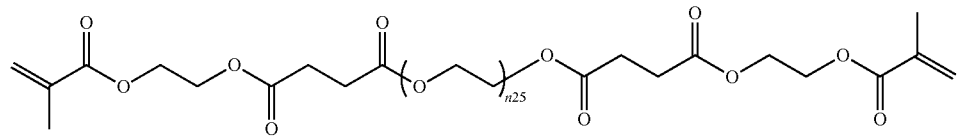

n25 being 1 to 300 (e.g., 1 to 200 and 1 to 100)

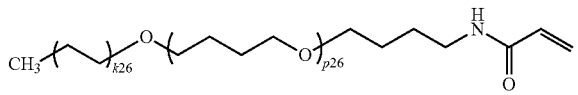

k26 being 4 to 25 (e.g., 6 to 25 and 2 to 10) and p26 being 2 to 20 (e.g., 6 to 18 and 2 to 8)

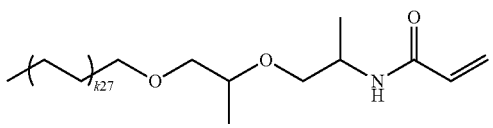

k27 being 2 to 24 (e.g., 4 to 24 and 4 to 18)

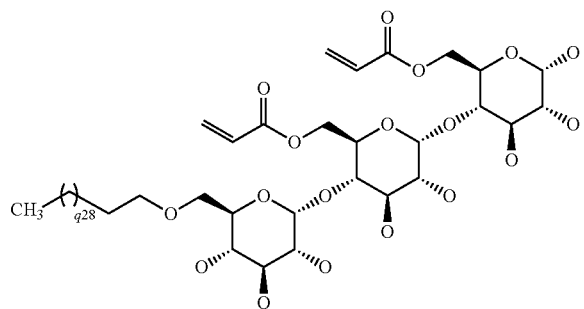

q28 being 1 to 40 (e.g., 6 to 40 and 6 to 20)

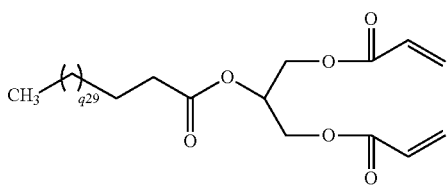

q29 being 1 to 40 (e.g., 6 to 40 and 6 to 20)

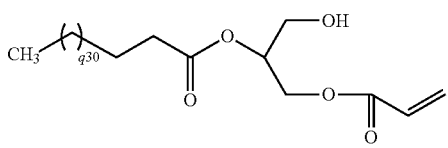

q30 being 1 to 40 (e.g., 6 to 40 and 6 to 20)

The instant malodor counteractive compositions can be used in a variety of forms and in a variety of products. Advantageously, the instant compositions are reactive against potent malodor ingredients while not affecting the odor of a fragrance or final product. Furthermore, these compositions and the methods herein can be pursued in any situation where malodor is present. In this respect, the present invention also features a method for counteracting amine- and thiol-based malodors of consumer, industrial and textile products, as well as the surrounding environment, by introducing or adding one or more malodor counteractant compositions of the invention to a consumer, industrial or textile product so that thiol- or amine-based malodors of the product are counteracted.

For the purposes of the present invention, a composition counteracts a malodor if it measurably (either qualitatively or quantitatively) reduces the presence of a malodor. In particular embodiments, a composition of the invention reduces the presence of an amine- and thiol-based malodor of a product by 50-100% as compared to a product that does not have the malodor counteracting composition.

In embodiments where the instant composition is intended to target a thiol-based malodor, it is particular advantageous to add an amine or other base including Lewis acids and Brønsted acids to accelerate the reactivity of the thiols with an α,β-unsaturated carbonyl compound contained in a composition of this invention. An example of a suitable Brønsted acid is bis(trifluoromethanesulfon)imide, which has been shown to catalyze the addition of thiols to α,β-unsaturated ketones, alkylidene malonates and acrylimides (see Wabnitz & Spencer, Organic Lett. (2003), 5, 2141-44). In some embodiments, the amine is already a component of the consumer, industrial or textile product. In other embodiments, the amine is an additional component added with the α,β-unsaturated carbonyl compound of the invention. Amines of use in the instant invention include, but are not limited to primary aliphatic amines, secondary aliphatic amines, tertiary aliphatic amines, aromatic amines, and heterocyclic amines. As is conventional in the art, a primary aliphatic amine is composed of one alkyl substituent bound to N together with two hydrogen atoms. Examples of primary aliphatic amines include methylamine, ethanolamine (2-aminoethanol), and the buffering agent tris. Secondary amines have two alkyl substituents bound to nitrogen together with one hydrogen atom. Examples of secondary aliphatic amines include dimethylamine and methylethanolamine. In tertiary amines, all three hydrogen atoms are replaced by organic substituents. Examples include trimethylamine. An aromatic amine is an amine with an aromatic substituent (i.e., —$NH_2$, —NH— or nitrogen group(s) attached to an aromatic hydrocarbon) whose structure usually contains one or more benzene rings. Examples of aromatic amines include, but are not limited to, aniline, toluidine, 2,4,6-trimenthylaniline, and anisidine. A heterocyclic amine is a compound containing at least one heterocyclic ring, which by definition has atoms of at least two different elements, wherein at least one of the atoms of the ring is a nitrogen atom. Examples of heterocyclic amines include, but are not limited to, indoles, skatoles, piperidines, morpholines, quinolines, quinoxalines, and pyridines.

Malodors particularly targeted by the instant molecules include amine- and thiol-based malodor such as bathroom odors, sweat, food odors, textile odors, home care and personal care product base odors, adhesive odors, and paint odors. In this respect, the instant compositions can be added to air refresheners, fabric refresheners, bar soaps, perfumes, fragrances, cologne, bath or shower gels, shampoos or other hair care products, cosmetic preparations, body odorants, deodorants, antiperspirants, liquid or solid fabric detergents or softeners, bleach products, disinfectants or all-purpose household or industrial cleaners, food, or industrial or textile products such as adhesives, paints, coatings, or textiles. In yet another embodiment, one or more of the instant compositions are used as part of a delivery system or polymer system to deliver a fragrance or compound of interest (e.g., a pharmaceutical).

Delivery Systems

Suitable delivery systems include microcapsules, emulsions, and polymeric particles.

Microcapsules containing active material (e.g., a fragrance, flavor, and malodor counteractant) is known in the art, see for example U.S. Pat. Nos. 2,800,457, 3,870,542, 3,516,941, 3,415,758, 3,041,288, 5,112,688, 6,329,057, 6,261,483, U.S. Pat. Appl. Nos. 2014/0044761 and 2014/0287008. Preferred encapsulating polymers include those formed from, acrylates, acrylamide, acrylate-co-acrylamide, melamine-formaldehyde or urea-formaldehyde condensates, as well as similar types of aminoplasts. Other wall forming materials include, polysiloxanes, polyamide, polyimide, polyvinyl alcohol, polyanhydride, polyolefin, polysulfone, polysaccharide, protein, polylactide (PLA), polyglycolide (PGA), polyorthoester, polyphosphazene, silicone, lipid, modified cellulose, gums, polystyrene, and polyesters or combinations of these materials. Other polymeric materials that are functional are ethylene maleic anyhydride copolymer, styrene maleic anhydride copolymer, ethylene vinyl acetate copolymer, and lactide glycolide copolymer. Biopolymers that are derived from alginate, chitosan, collegen, dextran, gelatin, and starch can also be used as the encapsulating materials. Additionally, microcapsules can be made via the simple or complex coacervation of gelatin.

Additional exemplary delivery systems include polymer-assisted delivery compositions (see U.S. Pat. No. 8,187,580), fiber-assisted delivery compositions (US 2010/0305021), cyclodextrin host guest complexes (U.S. Pat. No. 6,287,603 and US 2002/0019369), pro-fragrances (WO 2000/072816 and EP 0 922 084), and any combination thereof. Specific examples are (i) polymer matrix delivery systems such as melt extruded flavor/fragrance and spray dry encapsulation (US 2014/0205713); (ii) cyclodextrin delivery system; (iii) pro-perfume including reaction products of a primary/secondary amine, aromatic or non-aromatic imines (Schiff bases), oxazolidines, beta-keto esters, orthoesters, compounds comprising one or more beta-oxy or beta-thio carbonyl moieties capable of releasing a perfume (e.g., an alpha, beta-unsaturated ketone, aldehyde or carboxylic ester).

Emulsions and liquid formulation can be another form of formulation for the malodor counteractive composition of this this invention. See U.S. Pat. No. 5,283,056, U.S. Pat. No. 5,320,863, US 2006/0078527, US 2014/0147569, and WO 2014/085287.

Suitable active materials are described in US 2014/0287008. Examples include flavors, fragrance ingredients such as fragrance oils, taste masking agents, taste sensates, malodor counteractants (i.e., malodor counteractive agents and malodor control agents), vitamins, dyes, colorants, pigments, anti-inflammatory agents, anesthetics, analgesics, anti-fungal agents, antibiotics, anti-viral agents, anti-parasitic agents, anti-infectious/anti-acne agents, dermatological active ingredients, enzymes and co-enzymes, skin whitening agents, anti-histamines, chemotherapeutic agents, insect repellents, sunscreen actives, core modifiers, and sacrificial core ingredients. These active materials are optionally added, either as a free oil or in a microcapsules, to the malodor composition of this invention.

Deposition aids can also be included in the malodor counteractive composition of this invention. They are added to assist the deposition of the malodor counteractants to surfaces such as fabric, hair or skin. Examples include but are not limited to anionically, cationically, nonionically, or zwitterionically charged water-soluble polymers. See US 2014/0017287 and US 2013/0337023.

Applications

The delivery system of the present invention are well-suited for use, without limitation, in the following products:

a. Household products
   i. Liquid or Powder Laundry Detergents which can use the present invention include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818
   ii. Unit Dose Pouches, Tablets and Capsules such as those described in EP 1 431 382 A1, US 2013/0219996 A1, US 2013/0284637 A1, and U.S. Pat. No. 6,492,315. These unit dose formulations can contain high concentrations of a functional material (e.g., 5-100% fabric softening agent or detergent active), fragrance (e.g., 0.5-100%, 0.5-40%, and 0.5-15%), and flavor (e.g., 0.1-100%, 0.1-40%, and 1-20%). They can contain no water to limit the water content as low as less than 30% (e.g., less than 20%, less than 10%, and less than 5%).
   iii. Scent Boosters such as those described in US 2007/0269651 A1 and US2014/0107010 A1,
   iv. Fabric Care Products such as Rinse Conditioners, Fabric Liquid Conditioners, Tumble Drier Sheets, Fabric Refreshers, Fabric Refresher Sprays, Ironing Liquids, and Fabric Softener Systems such as those described in U.S. Pat. Nos. 6,335,315, 5,674,832, 5,759,990, 5,877,145, 5,574,179, 5,562,849, 5,545,350, 5,545,340, 5,411,671, 5,403,499, 5,288,417, 4,767,547 and 4,424,134
   v. Liquid dish detergents such as those described in U.S. Pat. Nos. 6,069,122 and 5,990,065
   vi. Automatic Dish Detergents such as those described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562
   vii. All-purpose Cleaners
   viii. Bathroom Cleaners
   ix. Bath Tissue
   x. Rug Deodorizers
   xi. Candles
   xii. Room Deodorizers
   xiii. Floor Cleaners
   xiv. Disinfectants
   xv. Window Cleaners
b. Household Devices
   i. Paper towels
   ii. Disposable Wipes
c. Baby Care Products
   i. Diaper Rash Cream/Balm
   ii. Baby Powder
d. Baby Care Devices
   i. Diapers
   ii. Bibs
   iii. Wipes
e. Oral Care Products. Tooth care products (as an example of preparations according to the invention used for oral care) generally include an abrasive system (abrasive or polishing agent), for example silicic acids, calcium carbonates, calcium phosphates, aluminum oxides and/or hydroxylapatites, surface-active substances, for example sodium lauryl sulfate, sodium lauryl sarcosinate and/or cocamidopropylbetaine, humectants, for example glycerol and/or sorbitol, thickening agents, for example carboxymethyl cellulose, polyethylene glycols, carrageenan and/or Laponite®, sweeteners, for example saccharin, taste correctors for unpleasant taste sensations, taste correctors for further, normally not unpleasant taste sensations, taste-modulating substances (for example inositol phosphate, nucleotides such as guanosine monophosphate, adenosine monophosphate or other substances such as sodium glutamate or 2-phenoxypropionic acid), cooling active ingredients, for example menthol derivatives, (for example L-menthyllactate, L-menthylalkylcarbonates, menthone ketals, menthane carboxylic acid amides), 2,2,2-trialkylacetic acid amides (for example 2,2-diisopropylpropionic acid methyl amide), icilin and icilin derivatives, stabilizers and active ingredients, for example sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan, cetylpyridinium chloride, aluminum lactate, potassium citrate, potassium nitrate, potassium chloride, strontium chloride, hydrogen peroxide, flavorings and/or sodium bicarbonate or taste correctors.

i. Tooth Paste. An exemplary formulation as follows:
1. calcium phosphate 40-55%
2. carboxymethyl cellulose 0.8-1.2%
3. sodium lauryl sulfate 1.5-2.5%
4. glycerol 20-30%
5. saccharin 0.1-0.3%
6. flavor oil 1.0-2.5%
7. water q.s. to 100%
   A typical procedure for preparing the formulation includes the steps of (i) mixing by a blender according to the foregoing formulation to provide a toothpaste, and (ii) adding a composition of this invention and blending the resultant mixture till homogeneous.
ii. Tooth Powder
iii. Oral Rinse
iv. Tooth Whiteners
v. Denture Adhesive
f. Hand Sanitizer
g. Antiinflammatory balms, ointment or spray
h. Health Care Devices
   i. Dental Floss
   ii. Toothbrushes
i. Feminine Hygiene Products such as Tampons, Feminine Napkins and Wipes, and Pantiliners
j. Personal Care Products: Cosmetic or pharmaceutical preparations, e.g., a "water-in-oil" (W/O) type emulsion, an "oil-in-water" (O/W) type emulsion or as multiple emulsions, for example of the water-in-oil-in-water (W/O/W) type, as a PIT emulsion, a Pickering emulsion, a micro-emulsion or nano-emulsion; and emulsions which are particularly preferred are of the "oil-in-water" (O/W) type or water-in-oil-in-water (W/O/W) type. More specifically,
   i. Personal Cleansers (Bar Soap, Body Wash, Shower Gel)
   ii. Sunscreen (Spray or lotion)
   iii. Deodorants and Antiperspirants including aerosol antiperspirant, stick antiperspirant, roll-on antiperspirant, emulsion spray antiperspirant, clear emulsion stick antiperspirant, soft solid antiperspirant, emulsion roll-on antiperspirant, clear emulsion stick antiperspirant, opaque emulsion stick antiperspirant, clear gel antiperspirant, clear stick deodorant and spray deodorant.
   iv. Wax-based Deodorant. An exemplary formulation as follows:
      1. Parafin Wax 10-20%
      2. Hydrocarbon Wax 5-10%
      3. White Petrolatum 210-15%
      4. Acetylated Lanolin Alcohol 2-4%
      5. Diisopropyl Adipate 4-8%
      6. Mineral Oil 40-60%
      7. Preservative (as needed)
         The formulation is prepared by (i) mixing the above ingredients, (ii) heating the resultant composition to 75° C. until melted, (iii) with stirring, adding 4% cryogenically ground polymer containing a fragrance while maintaining the temperature 75° C., and (iv) stirring the resulting mixture in order to ensure a uniform suspension while a composition of this invention is added to the formulation.
   v. Glycol/Soap Type Deodorant. An exemplary formulation as follows:
      1. Propylene Glycol 60-70%
      2. Sodium Stearate 5-10%
      3. Distilled Water 20-30%
      4. 2,4,4-Trichloro-2'-Hydroxy Diphenyl Ether, manufactured by the Ciba-Geigy Chemical Company and a Trademark of the Ciba-Geigy Chemical Company) 0.01-0.5%
         The ingredients are combined and heated to 75° C. with stirring until the sodium stearate has dissolved. The resulting mixture is cooled to 40° C. followed by addition of a composition of this invention.
   vi. Lotion including Body Lotion, Facial Lotion, and Hand Lotion
   vii. Body Powder
   viii. Hand Sanitizers
   ix. Toiletries
   x. Body Spray
   xi. Shave Cream
   xii. Bath Soak
   xiii. Exfoliating Scrub
k. Personal Care Devices
   i. Facial Tissues
   ii. Cleansing wipes
l. Hair Care Products
   i. Shampoo (liquid and dry powder)
   ii. Hair Conditioner (Rinse out and leave-in)
   iii. Hair Rinses
   iv. Hair Refreshers
   v. Hair styling products, Hair Fixative and styling aids
   vi. Hair combing creams
   vii. Hair Bleaches, Dyes and Colorants
m. Beauty Care
   i. Fine Fragrance—Alcoholic. Compositions and methods for incorporating fragrance capsules into alcoholic fine fragrances are described in U.S. Pat. No. 4,428,869. Alcoholic fine fragrances may contain the following:
      1. Ethanol (1-99%)
      2. Water (0-99%)
      3. A suspending aide including but not limited to: hydroxypropyl cellulose, ethyl cellulose, silica, microcrystalline cellulose, carrageenan, propylene glycol alginate, methyl cellulose, sodium carboxymethyl cellulose or xanthan gum (0.-1-%)
      4. Optionally an emulsifier or an emollient may be included including but not limited to those listed above
   ii. Solid Perfume
   iii. Liquid Foundation
   iv. Powder Foundation
   v. Eye Shadow
   vi. Lipstick/lip balm
n. Confectioneries, preferably selected from the group consisting of chocolate, chocolate bar products, other products in bar form, fruit gums, hard and soft caramels and chewing gum
   i. Gum
      1. Gum base (natural latex chicle gum, most current chewing gum bases also presently include elastomers, such as polyvinylacetate (PVA), polyethylene, (low or medium molecular weight) polyisobutene (PIB), polybutadiene, isobutene-isoprene copolymers (butyl rubber), polyvinylethylether (PVE), polyvinylbutyether, copolymers of vinyl esters and vinyl ethers, styrene-butadiene copolymers (styrene-butadiene rubber, SBR), or vinyl elastomers, for example based on vinylacetate/vinyllaurate, vinylacetate/vinylstearate or ethylene/vinylacetate, as well as mixtures of the mentioned elastomers, as described for example in EP 0 242 325, U.S. Pat. No.

4,518,615, U.S. Pat. No. 5,093,136, U.S. Pat. No. 5,266,336, U.S. Pat. No. 5,601,858 or U.S. Pat. No. 6,986,709.) 20-25%
2. Powdered sugar 45-50%
3. glucose 15-17%
4. starch syrup 10-13%
5. plasticizer 0.1%
6. flavor 0.8-1.2%

The components described above were kneaded by a kneader according to the foregoing formulation to provide a chewing gum. Encapsulated Flavor or sensate is then added and blended till homogeneous.
   ii. Breath Fresheners
   iii. Orally Dissolvable Strips
   iv. Chewable Candy
   v. Hard Candy
o. Baked products, preferably selected from the group consisting of bread, dry biscuits, cakes and other cookies;
p. snack foods, preferably selected from the group consisting of baked or fried potato chips or potato dough products, bread dough products and corn or peanut-based extrudates;
   i. Potato, tortilla, vegetable or multigrain chips
   ii. Popcorn
   iii. Pretzels
   iv. Extruded stacks
q. Cereal Products preferably selected from the group consisting of breakfast cereals, muesli bars and precooked finished rice products
r. Alcoholic and non-alcoholic beverages, preferably selected from the group consisting of coffee, tea, wine, beverages containing wine, beer, beverages containing beer, liqueurs, schnapps, brandies, sodas containing fruit, isotonic beverages, soft drinks, nectars, fruit and vegetable juices and fruit or vegetable preparations; instant beverages, preferably selected from the group consisting of instant cocoa beverages, instant tea beverages and instant coffee beverages
   i. Ready to drink liquid drinks
   ii. Liquid Drink Concentrates
   iii. Powder Drinks
   iv. Coffee: Instant Cappucino
      1. Sugar 30-40%
      2. Milk Powder 24-35%
      3. Soluble Coffee 20-25%
      4. Lactose 1-=15%
      5. Food Grade Emulsifier 1-3%
      6. Encapsulated Volatile Flavor 0.01-0.5%
   v. Tea
   vi. Alcoholic
s. Spice blends and consumer prepared foods
   i. Powder gravy, sauce mixes
   ii. Condiments
   iii. Fermented Products
t. Ready to heat foods: ready meals and soups, preferably selected from the group consisting of powdered soups, instant soups, precooked soups
   i. Soups
   ii. Sauces
   iii. Stews
   iv. Frozen entrees
u. Dairy Products milk products, preferably selected from the group consisting of milk beverages, ice milk, yogurt, kefir, cream cheese, soft cheese, hard cheese, powdered milk, whey, butter, buttermilk and partially or fully hydrolyzed milk protein-containing products Flavored milk beverages
   i. Yoghurt
   ii. Ice cream
   iii. Bean Curd
   iv. Cheese
v. Soya protein or other soybean fractions, preferably selected from the group consisting of soya milk and products produced therefrom, soya lecithin-containing preparations, fermented products such as tofu or tempeh or products produced therefrom and soy sauces;
w. meat products, preferably selected from the group consisting of ham, fresh or raw sausage preparations, and seasoned or marinated fresh or salt meat products
x. Eggs or egg products, preferably selected from the group consisting of dried egg, egg white and egg yolk
y. and oil-based products or emulsions thereof, preferably selected from the group consisting of mayonnaise, remoulade, dressings and seasoning preparations
z. fruit preparations, preferably selected from the group consisting of jams, sorbets, fruit sauces and fruit fillings; vegetable preparations, preferably selected from the group consisting of ketchup, sauces, dried vegetables, deep-frozen vegetables, precooked vegetables, vegetables in vinegar and preserved vegetables.

The above-listed applications are all well known in the art. For example, fabric softener systems are described in U.S. Pat. Nos. 6,335,315, 5,674,832, 5,759,990, 5,877,145, 5,574,179; 5,562,849, 5,545,350, 5,545,340, 5,411,671, 5,403,499, 5,288,417, and 4,767,547, 4,424,134. Liquid laundry detergents include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818. Liquid dish detergents are described in U.S. Pat. Nos. 6,069,122 and 5,990,065. Shampoo and conditioners that can employ the present invention include those described in U.S. Pat. Nos. 6,162,423, 5,968,286, 5,935,561, 5,932,203, 5,837,661, 5,776,443, 5,756,436, 5,661,118, 5,618,523, 5,275,755, 5,085,857, 4,673,568, 4,387,090 and 4,705,681. Automatic Dish Detergents are described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562.

All parts, percentages and proportions refer to herein and in the claims are by weight unless otherwise indicated.

The values and dimensions disclosed herein are not to be understood as being strictly limited to the exact numerical values recited. Instead, unless otherwise specified, each such value is intended to mean both the recited value and a functionally equivalent range surrounding that value. For example, a value disclosed as "50%" is intended to mean "about 50%."

The term "polymer" includes oligomers having 2-10 repeated units and macromolecules having 11 or more repeated units.

The invention is described in greater detail by the following non-limiting examples.

Example 1

A composition of this invention, i.e., Composition 1 was prepared following the procedure below. This composition containing a malodor counteractant having the following formula:

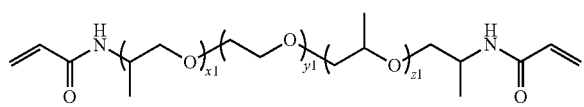

y1 being 12.5 and x1+z1 being 6.

Jeffamine ED-900 was the source for the backbone of this malodor counteractant. Jeffamine ED-900 is a polyetheramine commercially available from Huntsman Corporation (Texas, USA) having the following formula:

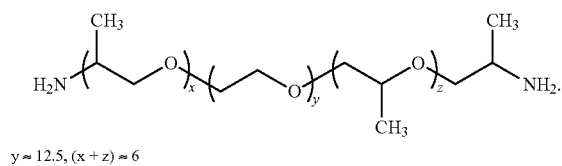

$y \approx 12.5, (x+z) \approx 6$

It is water soluble, with an approximate molecular weight of 900.

Jeffamine ED-900 was first dissolved in methylene chloride (250 mL). Triethylamine (11.8 g) was then added under nitrogen atmosphere at −10° C. To the resultant mixture was added acryloyl chloride ($CH_2$=CHCOCl, 10.6 g) was added drop-wise. After completion of the addition, the reaction mixture was warmed to room temperature and stirred for 5 hours. After the reaction, the triethylammonium chloride salt formed therein was filtered and a filtrate was collected. To the filtrate was added 0.2 g of Stabiliff (i.e., methyl 3-(3,5-di-tert-butyl-4-hydroxyphenyl)propanoate, a stabilizer) and 300 mL of ethanol to perform solvent exchange. The resultant mixture was refluxed in a 1 L 3-necked flask with a bidwell set-up until all methylene chloride was removed as determined by NMR spectroscopy. The thus obtained Composition 1 had a solid percentage of 72 wt % as determined by thermogravimetric analysis (TGA). The percent capping (i.e., the percentage of the amine groups that react and form acrylamide function groups) was determined to be >95% by NMR spectroscopy.

Example 2

Composition 2 was prepared following a procedure similar to that of Composition 1 described above.

The starting material for preparing Composition 2 is Jeffamine ED-2003 having the following formula:

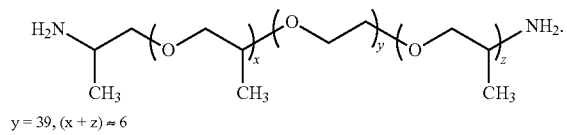

$y = 39, (x+z) \approx 6$

This compound is water soluble and has a molecular weight of 2000.

Jeffamine ED-2003 (50 g; Huntsman) was first dissolved in methylene chloride (250 mL). Triethylamine (5.1 g) was subsequently added under nitrogen atmosphere at −10° C. To the mixture acryloyl chloride (4.6 g) was added drop-wise to the stirring mixture. After addition, the reaction mixture was warmed to room temperature and stirred for 5 hours. The triethylammonium chloride salt was filtered off. After 0.2 g Stabiliff and 300 mL ethanol was added, the resultant mixture was refluxed in a 1 L 3-necked flask and bidwell set-up until all the methylene chloride was removed determined by NMR spectroscopy. The thus prepared Composition 2 had a solid content of 44% as determined by TGA. The percent capping was determined to be >95% by NMR spectroscopy.

Example 3

Composition 3 was prepared following a procedure similar to that of Composition 1 described above.

The starting material for preparing Composition 3 was Jeffamine EDR-176 having the following formula:

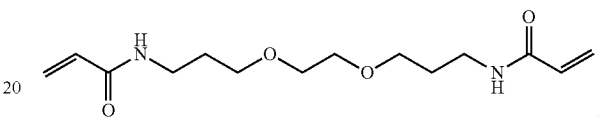

This compound is water soluble and has a molecular weight of 284.

Jeffamine EDR-176 (50 g; Huntsman) was first dissolved in methylene chloride (250 mL). Triethylamine (58.1 g) was then added under nitrogen atmosphere at −10° C. To the resultant mixture was added acryloyl chloride (51.9 g). After addition, the reaction mixture was warmed to room temperature and was stirred for 5 hours. Triethylammonium chloride salt was filtered off. Stabiliff (0.2 g) and ethanol 9300 mL) were added in order to perform solvent exchange. The mixture was refluxed in a 1 L 3-necked flask and bidwell set-up until all the methylene chloride was removed as determined by NMR spectroscopy. Composition 3 this prepared had a solid content of 49% as determined by TGA. The percent capping was determined to be >95% by NMR spectroscopy.

Example 4

Composition 4 was prepared following a procedure similar to that of Composition 1 described above.

The starting material for preparing Composition 3 was polyethylene glycol (PEG) having the following formula:

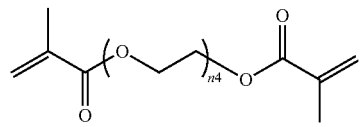

This compound is water soluble and has a molecular weight of 2000.

PEG (30 g; Sigma-Aldrich) was first dissolved in 250 mL of methylene chloride. Triethylamine (2 g) was then added under nitrogen atmosphere at −10° C. To the mixture was added acryloyl chloride (3.6 g). After addition, the reaction mixture was warmed to room temperature and stirred overnight. The reaction mixture was then washed with 100 g of 2M $Na_2CO_3$ aqueous solution. The organic layer was dried over anhydrous $MgSO_4$ and filtered. Composition 4 was precipitated out in 9:1 (v/v) diethyl ether/hexanes, collected and dried under vacuum at 40° C. The percent capping was determined to be near completion by NMR spectroscopy.

Example 5

Composition 5 was prepared following the procedure below.

More specifically, to a freshly prepared Composition 1 was added 420 g of ion-exchange resin and the mixture was agitated to allow the reaction mass to equilibrate for 2 hours at room temperature. The solution was vacuum filtered and Composition 5 was obtained as the filtrate.

Composition 5 was analyzed with HPLC using UV detection. Acrylic acid was found to be present at a level of 250 ppm or less (e.g., 211 ppm). As a comparison, Composition 1 had an acrylic acid level of 2332 ppm.

Malodor Counteracting Performance 1. nBA Headspace Reactivity

Compositions 1 and 3 were tested for neutralizing n-butylamine (nBA) following the procedure below.

To generate the malodor vapor for headspace reactivity, 2.5 g of nBA was added to a 8 oz. jar which was then capped with a septa screw cap and allowed to equilibrate. Composition 1 or 3 (0.1 g) was placed into three 20-mL headspace vials and capped. Two additional empty vials were prepared and capped as controls. 800 μL of the malodor vapor was dispensed into the vials using syringe, starting and ending with the control vial, at a rate of 15 mL/min. The resulting mixture was allowed to equilibrate for 1 hour, at which point analyzed by a gas chromatography-mass selective detector (GC-MSD) for malodor counteracting reactivity. Jeffamine ED-900 and Jeffamine EDR-176, the respective backbone of Compositions 1 and 3, were used as controls in separate headspace vials.

Unexpectedly, all nBA was counteracted by Compositions 1 and 3 (i.e., reduced by 100%). As a contrast, nBA As shown in Table 1, reduction of nBA by Jeffamine ED-900 and EDR-176 was only 50% and 55%, respectively.

2. Malodor Absorption

Composition 3 was evaluated for malodor counteracting activity following the procedure below.

To generate the malodor vapor for absorption, 5% of the malodor solution consisting of various ingredients were prepared in mineral oil was added to a 1 L POP flask and equilibrated overnight with constant stirring to prepare the malodor headspace. Composition 3 (0.5 g) was added to 3×8 oz. sample jar and was allowed to dry down overnight to produce a thin film. The jar was then tightly capped with a lid set-up. 60 mL of the malodor vapor was transferred to a sample jar via syringe allowing 3 minutes intervals in between. The jar was allowed to equilibrate for 30 min. 100 mL of the headspace was collected from each jar onto a tenax tube using low flow pump at 50 mL/min, at which point analyzed by a gas chromatography/flame ionization detector (GC-FID). Jeffamine EDR-176 was used as control in a separate sample jar. The reduction of three malodor compounds were analyzed: 2,6-dimethyl pyridine (DMP), 2-ethyl-3-methyl pyrazine (EMP), and dibutyl sulfide (DBS). Note that DMP and EMP are amine-based malodors and DBS is a sulfur-based malodor. Unexpectedly, Composition 3 reduced DMP by 54%, EMP by 58% and DBS by 13%. While Jefferamine EDR-176 did not reduce any of these malodors.

3. Stability by NMR Spectroscopy

The stability of Composition 3 was determined by $^1$H-NMR. Composition 3 was dried and re-dissolved in deuterium oxide ($D_2O$). 2.5 equivalence of 0.025 M n-butyamine (nBA) in $D_2O$ was then added. The mixture was allowed to react and was monitored overtime by $^1$H-NMR spectroscopy. Composition 3 was shown stable for 96 hours. No hydrolysis was observed by $^1$H-NMR during this period.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Indeed, to prepare an effective malodor counteracting composition, one skilled in the art can select a suitable counteractant and stabilizer. Further, the contents of the components and their ratio can also be determined by a skilled artisan through assays known in the art.

From the above description, a skilled artisan can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A malodor counteracting composition comprising a malodor counteractant that is capable of neutralizing a malodor and a stabilizer that is methyl-3-(3,5-di-tert-butyl-4-hydroxyphenyl)propanoate, wherein the malodor counteractant has a backbone and one or more reactive end groups that are covalently attached to the backbone, the backbone has a molecular weight of 100 to 50,000 Daltons, the backbone is selected from the group consisting of a poly(ethylene oxide), poly(propylene oxide), poly(ethylene oxide-co-propylene oxide), and combinations thereof, and the one or more reactive end groups each have an α,β-unsaturated carbonyl group.

2. The malodor counteracting composition of claim 1, further comprising an end solvent selected from the group consisting of ethanol, methanol, ethyl acetate, propylene glycol, diphenyl phthalate, dipropylene glycol, tripropylene glycol, water, ethylene glycol, diethyl phthalate, 1-methoxy-2-propanol, 2-methoxy-1-methylethyl acetate, tripropylene glycol methyl ether, dipropylene glycol methyl ether, dipropylene glycol n-butyl ether, dipropylene glycol methyl ether acetate, triacetin, 1-methyl-4-isopropylidene-1-cyclohexene, 2-(4-methyl-1-cyclohex-3-enyl)propan-2-ol, and a combination thereof.

3. The malodor counteracting composition of claim 1, wherein the composition contains acrylic acid at a level of 2000 ppm or less.

4. The malodor counteracting composition of claim 1, wherein the α,β-unsaturated carbonyl group is an ionone moiety, an irone moiety, a damascone moiety, an acryloxy moiety, a methacryloxy moiety, an acrylamide moiety, a methacrylamide moiety, or a crotonate moiety.

5. The malodor counteracting composition of claim 4, wherein the α,β-unsaturated carbonyl group is an acryloxy moiety, a methacryloxy moiety, an acrylamide moiety, or a methacrylamide moiety.

6. The malodor counteracting composition of claim 1, wherein the malodor counteractant is a compound of Formula I:

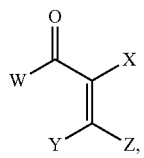

I in which each of W, X, Y, and Z, independently, is H, halo, nitro, cyano, $C_1$-$C_{10}$ alkyl, $C_1$-$C_{10}$ alkoxy, $C_2$-$C_{10}$ alkenyl, $C_2$-$C_{10}$ alkynyl, $C_3$-$C_{10}$ cycloalkyl, $C_1$-$C_{10}$ heterocycloalkyl, $C_1$-$C_{10}$alkylamino, $C_1$-$C_{20}$ dialkylamino, or -Q-P, provided that at least one of W, X, Y, and Z is-Q -P, P being a polymer moiety selected from the group consisting of a poly(ethylene oxide), poly(propylene oxide), poly(ethylene oxide-co-propylene oxide), and combinations thereof, Q being a bond, O, S, $NR^1$, or $CR^2R^3$, in which each of $R^1$, $R^2$, and $R^3$, independently, is H, halo, OH, nitro, cyano, $C_1$-$C_{10}$ alkyl, $C_1$-$C_{10}$ alkoxy, $C_2$-$C_{10}$ alkenyl, $C_2$-$C_{10}$ alkynyl, $C_3$-$C_{10}$ cycloalkyl, $C_1$-$C_{10}$heterocycloalkyl, $C_1$-$C_{10}$ alkylamino, or $C_1$-$C_{20}$ dialkylamino; $R^1$ together with the nitrogen atom to which it attaches is a $C_1$-$C_{10}$ heterocycloalkyl or heteroaryl; or $R^2$ and $R^3$, together with the carbon atom to which they are attached, are $C_3$-$C_{10}$ cycloalkyl, $C_1$-$C_{10}$heterocycloalkyl, aryl, or heteroaryl.

7. The malodor counteracting composition of claim 6, wherein Q is NH and P has an average molecular weight of 1,000 to 10,000.

8. The malodor counteracting composition of claim 6, wherein the composition contains acrylic acid at a level of 2000 ppm or less.

9. The malodor counteracting composition of claim 6, wherein each of X, Y, and Z, independently, is H or methyl.

10. The malodor counteracting composition of claim 9, wherein P is poly(ethylene oxide-co-propylene oxide) and has a molecular weight of 200 to 5000 Daltons.

11. A malodor counteracting composition comprising a malodor counteractant that is capable of neutralizing a malodor and a stabilizer that is methyl-3-(3,5-di-tert-butyl-4-hydroxyphenyl)propanoate, wherein the malodor counteractant is:

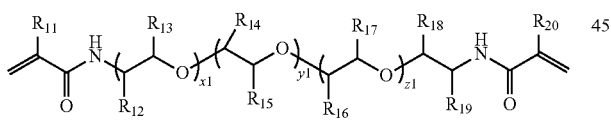

y1 being 1 to 50 and x1+z1 being 0 to 100
each of $R_{11}$, $R_{12}$, $R_{13}$, $R_{14}$, $R_{15}$, $R_{16}$, $R_{17}$, $R_{18}$, $R_{19}$, and $R_{20}$, independently,
being H, $CH_3$, or $CH_2CH_3$

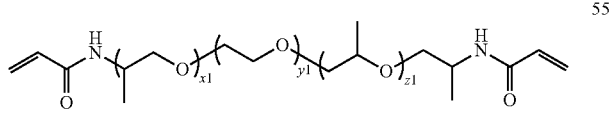

y1 being 1 to 50 and x1+z1 being 0 to 100

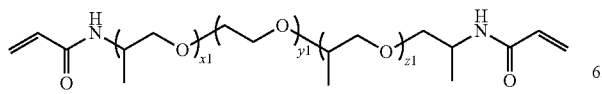

y1 being 1 to 50 and x1+z1 being 0 to 100

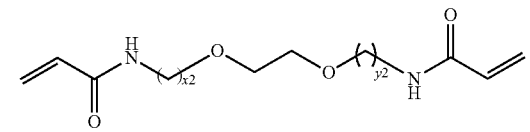

x2 being 0 to 50 and y2 being 0 to 50

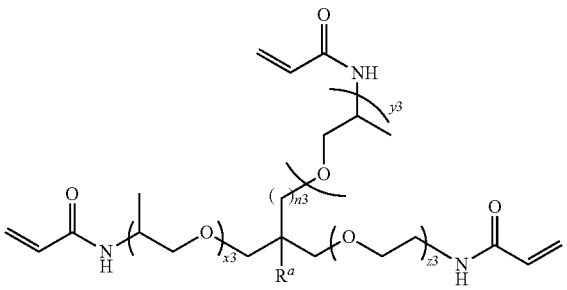

x3+y3+z3 being 1 to 200, n3 being 0 to 10, and $R^a$ being H, $CH_3$, or $C_2H_5$

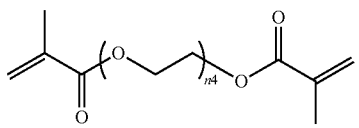

n4 being 1 to 400

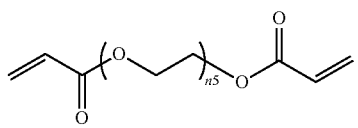

n5 being 1 to 400

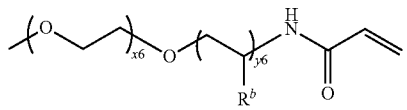

x6 being 1 to 80, y6 being 1 to 80, and $R^b$ being H, $CH_3$, or $CH_2CH_3$

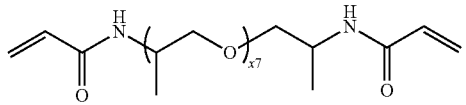

x7 being 1 to 80

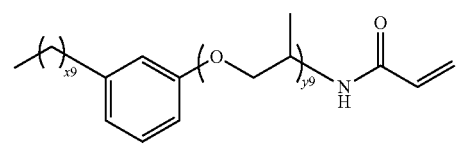

x9 being 1 to 18 and y9 being 5 to 25

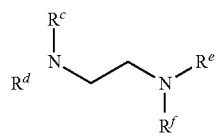
each of $R^c$, $R^d$, $R^e$, and $R^f$, independently, being
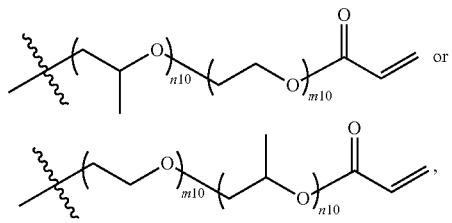
in which each of m10 and n10, independently, is 1 to 80
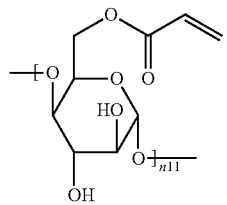
n11 being 10 to 100,000
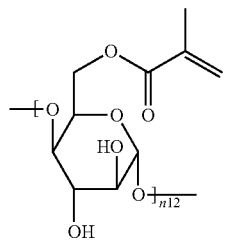
n12 being 10 to 100,000
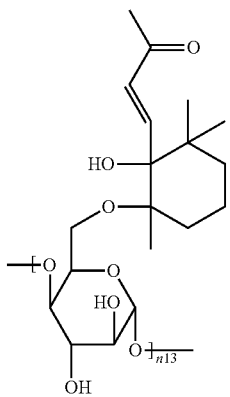
n13 being 10 to 100,000
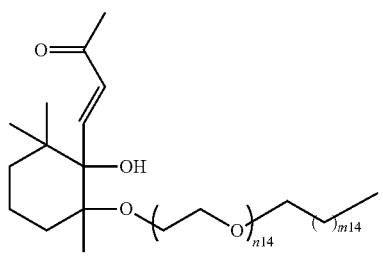
n14 being 1 to 80 and m14 being 4 to 24
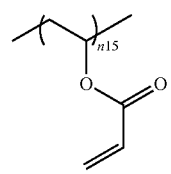
n15 being 300 to 40,000
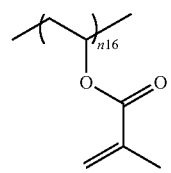
n16 being 300 to 40,000
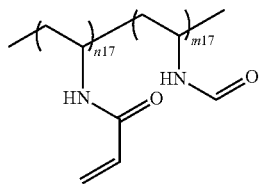
each of m17 and n17, independently, being 300 to 40,000
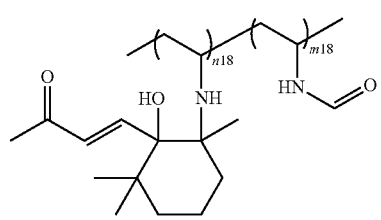
each of m18 and n18, independently, being 300 to 40,000
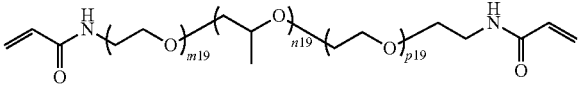
each of m19, n19, and p19, independently, being 1 to 100
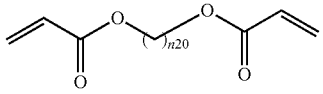
m20 being 6 to 24

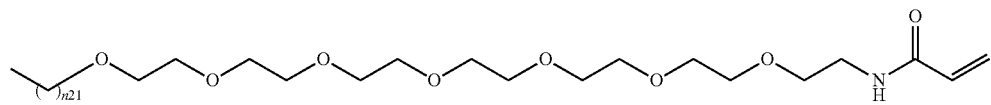
n21 being 10 to 50
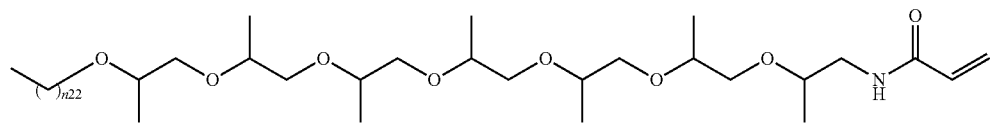
n22 being 14 to 50
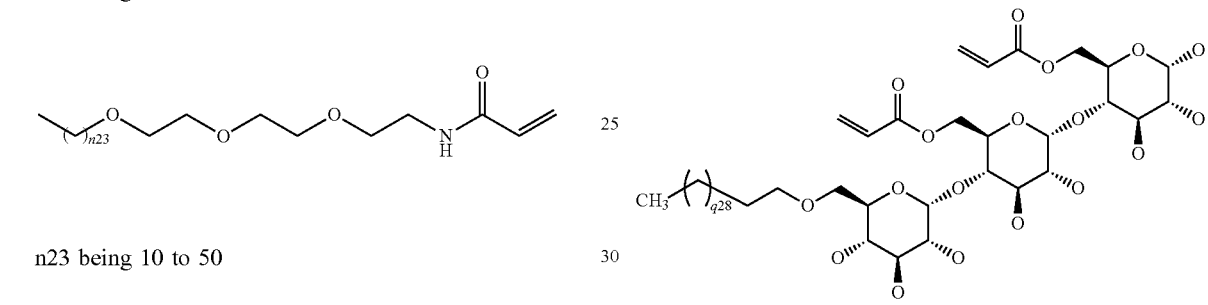
q28 being 1 to 40
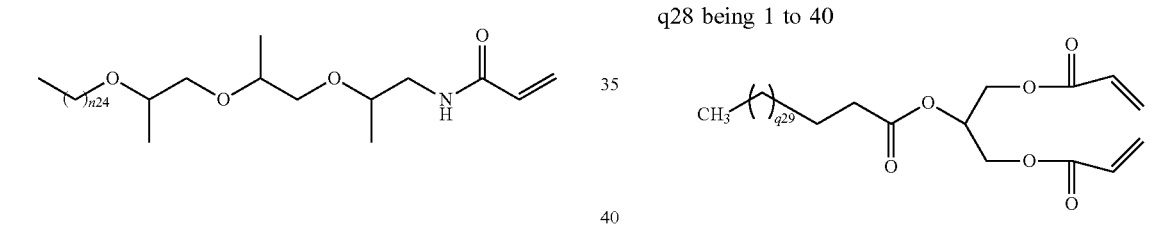
n23 being 10 to 50
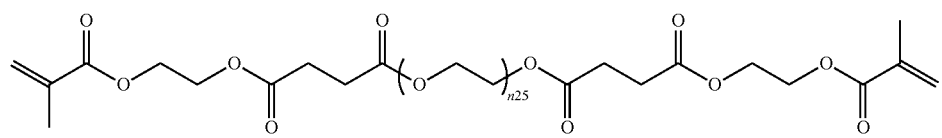
n24 being 10 to 50
q29 being 1 to 40
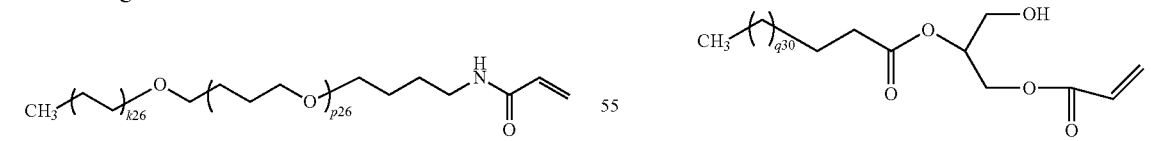
n25 being 1 to 300
q30 being 1 to 40.
12. The malodor counteracting composition of claim 11, wherein the counteractant is:
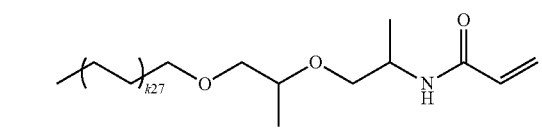
k26 being 4 to 25 and p26 being 2 to 20
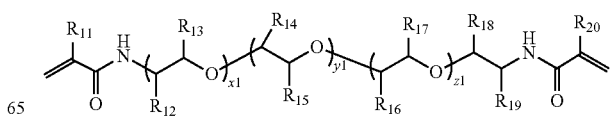
k27 being 2 to 24
y1 being 3 to 20 and x1 +z1 being 20 to 50 each of $R_{11}$, $R_{12}$, $R_{13}$, $R_{14}$, $R_{15}$, $R_{16}$, $R_{17}$, $R_{18}$, $R_{19}$, and $R_{20}$, independently,
being H, $CH_3$, or $CH_2CH_3$

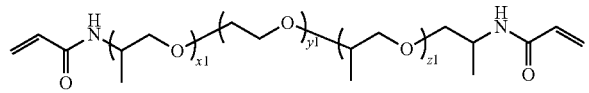

y1 being 3 to 20 and x1 +z1 being 20 to 50

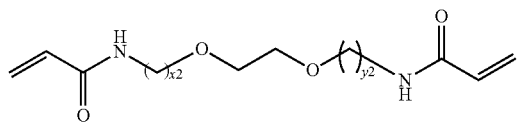

x2 being 2 to 12 and y2 being 2 to 12

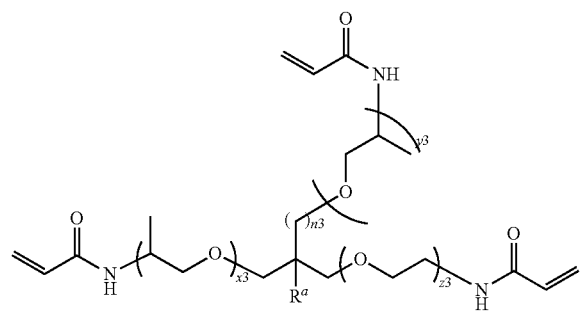

x3+y3+z3 being 50 to 120, n3 being 0 to 4, and $R^a$ being H, or $CH_3$

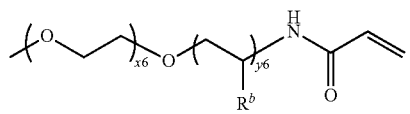

x6 being 4 to 50, y6 being 4 to 50, and $R^b$ being H, or $CH_3$

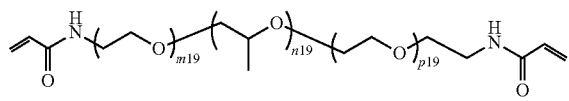

each of m19, n19, and p19, independently, being 4 to 40.

13. A method of neutralizing a malodor in a consumer, industrial or textile product, the method comprising the step of:
providing a malodor counteracting composition of claim 1, and
adding the malodor counteracting composition to a consumer, industrial or textile product so that the product is capable of neutralizing a malodor by using the malodor counteractant to react with or absorbing the malodor.

14. The method of claim 13, wherein the consumer, industrial, or textile product is a home care product, a fabric care product, or a personal care product.

15. The method of claim 13, wherein the malodor composition contains acrylic acid at a level of 2000 ppm or less.

16. A method of neutralizing a malodor in a consumer, industrial or textile product, the method comprising the step of:
providing a malodor counteractant of Formula I:

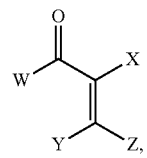

in which each of W, X, Y, and Z, independently, is H, halo, nitro, cyano, $C_1$-$C_{10}$ alkyl, $C_1$-$C_{10}$ alkoxy, $C_2$-$C_{10}$ alkenyl, $C_2$-$C_{10}$ alkynyl, $C_3$-$C_{10}$ cycloalkyl, $C_1$-$C_{10}$ heterocycloalkyl, $C_1$-$C_{10}$ alkylamino, $C_1$-$C_{20}$ dialkylamino, or -Q-P, provided that at least one of W, X, Y, and Z is -Q-P, P being a polymer moiety selected from the group consisting of a poly(ethylene oxide), poly(propylene oxide), poly(ethylene oxide-co-propylene oxide) and combinations thereof, Q being a bond, O, S, $NR^1$, or $CR^2R^3$, in which each of $R^1$, $R^2$, and $R^3$, independently, is H, halo, OH, nitro, cyano, $C_1$-$C_{10}$ alkyl, $C_1$-$C_{10}$ alkoxy, $C_2$-$C_{10}$ alkenyl, $C_2$-$C_{10}$ alkynyl, $C_3$-$C_{10}$ cycloalkyl, $C_1$-$C_{10}$ heterocycloalkyl, $C_1$-$C_{10}$ alkylamino, or $C_1$-$C_{20}$ dialkylamino; $R^1$, together with the nitrogen atom to which it attaches, is a $C_1$-$C_{10}$ heterocycloalkyl or heteroaryl; or $R^2$ and $R^3$, together with the carbon atom to which they are attached, are $C_3$-$C_{10}$ cycloalkyl, $C_1$-$C_{10}$ heterocycloalkyl, aryl, or heteroaryl; and adding the malodor counteractant and a stabilizer to a consumer, industrial or textile product so that the product is capable of neutralizing a malodor by using the malodor counteractant to react with or absorbing the malodor, wherein the stabilizer is methyl-3-(3,5-di-tert-butyl-4-hydroxyphenyl)propanoate.

17. A consumer, industrial, or textile product comprising a malodor counteracting composition of claim 1 at an amount effective to neutralize a malodor.

18. The consumer, industrial, or textile product of claim 17, wherein the product is a home care product, a fabric care product, or a personal care product.

19. The malodor counteracting composition of claim 1, wherein the counteractant is:

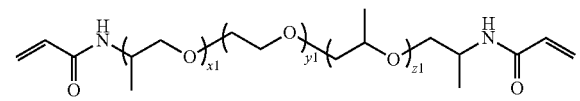

y1 being 1 to 50 and x1 +z1 being 0 to 100,

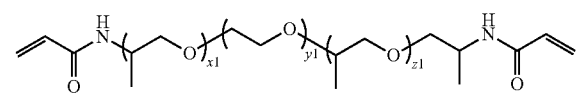

y1 being 1 to 50 and x1 +z1 being 0 to 100, or

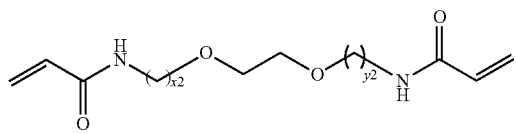
x2 being 0 to 50 and y2 being 0 to 50.
20. The malodor counteracting composition of claim 1, wherein the counteractant is:
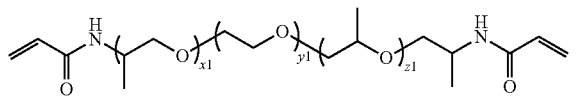
y1 being 12.5 and x1 +z1 being 6,
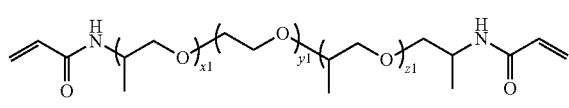
y1 being 39 and x1 +z1 being 6, or
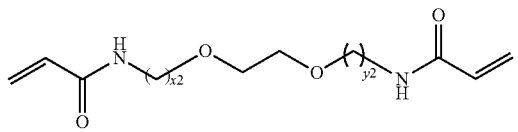
x2 being 3 and y2 being 3.
* * * * *